United States Patent [19]

Sullivan

[11] Patent Number: 4,891,101

[45] Date of Patent: Jan. 2, 1990

[54] PURIFICATION OF TERTIARY HYDROPEROXIDES CONTAINING PRIMARY AND SECONDARY HYDROPEROXIDE CONTAMINANTS

[75] Inventor: Carl J. Sullivan, Exton, Pa.

[73] Assignee: Arco Chemical Technology, Inc., Wilmington, Del.

[21] Appl. No.: 275,483

[22] Filed: Nov. 23, 1988

[51] Int. Cl.$^4$ .............................................. B01D 3/36
[52] U.S. Cl. ........................................ 203/36; 203/38; 203/43; 203/59; 203/60; 203/DIG. 6; 568/576
[58] Field of Search ................... 203/14, 36, 37, 43, 203/60, 59, DIG. 6, 38; 568/576

[56] References Cited

U.S. PATENT DOCUMENTS

| | | | |
|---|---|---|---|
| 3,449,217 | 6/1969 | Harvey | 203/6 |
| 3,864,216 | 2/1975 | Worrell et al. | 203/49 |
| 4,120,902 | 10/1978 | Wu | 568/576 |
| 4,381,222 | 4/1983 | Brossmann et al. | 203/33 |
| 4,408,083 | 10/1983 | Toyoura et al. | 568/576 |
| 4,584,413 | 4/1986 | Thornton et al. | 568/576 |

FOREIGN PATENT DOCUMENTS

| | | | |
|---|---|---|---|
| 0003083 | 7/1979 | European Pat. Off. | 568/576 |
| 0135295 | 3/1985 | European Pat. Off. | 568/576 |
| 3721785 | 2/1988 | Fed. Rep. of Germany | 568/576 |
| 1232710 | 5/1971 | United Kingdom | 568/576 |

OTHER PUBLICATIONS

Bouillon et al, The Chemistry of Peroxides, pp. 298-299, 308-309.
Everett et al., Trans. Far. Soc. 49, 410, 1953.

Primary Examiner—Virginia Manoharan
Attorney, Agent, or Firm—Stephen D. Harper

[57] ABSTRACT

Primary and secondary hydroperoxide contaminants in a tertiary hydroperoxide composition obtained by oxidation of a branched hydrocarbon are removed by contacting the tertiary hydroperoxide with a carboxylic acid derivative such as an anhydride and a basic compound such as sodium hydroxide. A tertiary hydroperoxide such as tertiary butyl hydroperoxide is purified with minimal loss of the desired tertiary hydroperoxide.

19 Claims, No Drawings

PURIFICATION OF TERTIARY HYDROPEROXIDES CONTAINING PRIMARY AND SECONDARY HYDROPEROXIDE CONTAMINANTS

This invention relates to the purification of tertiary hydroperoxides. In particular, the invention pertains to the selective removal of primary and secondary hydroperoxide impurities from tertiary hydroperoxide compositions produced by the oxidation of branched hydrocarbons. The process of this invention results in minimal loss of the desired tertiary hydroperoxide during purification.

Tertiary hydroperoxides are of value in a number of applications. Tertiary butyl hydroperoxide, obtained by the oxidation of isobutane, is an example of a tertiary hydroperoxide which has been found to be of particular commercial interest. Tertiary hydroperoxides may be used as reagents in the epoxidation of olefins and as intermediates in the preparation of free radical initiators for the polymerization of ethylenically unsaturated monomers. However, primary and secondary hydroperoxides are unavoidably formed in low concentrations during the oxidation process used to obtain the tertiary hydroperoxide. In certain applications, the performance of the tertiary hydroperoxide is adversely affected by the presence of the primary and secondary hydroperoxide contaminants. For example, in the preparation of peroxyesters from tertiary hydroperoxides for use as polymerization initiators, the acidity of the resulting peroxyester will tend to increase significantly in handling and storage and interfere with the performance of the peroxyester in its intended application if significant levels of primary and secondary hydroperoxides are present.

A number of methods are known for the purification of tertiary hydroperoxides produced by oxidation of branched hydrocarbons.

In one type of method, the tertiary hydroperoxide is separated from most of the oxidation by-products by fractional distillation. U.S. Pat. No. 3,449,217 describes such a distillation in the presence of a base to neutralize the oxidate mixture. U.S. Pat. No. 3,864,216 teaches an azeotropic distillation from water, using a diluent gas to avoid forming a flammable mixture during distillation. U.S. Pat. No. 4,381,222 teaches the distillative separation of tertiary alkyl hydroperoxides from the corresponding di-tertiary alkyl peroxides by neutralizing the mixture with base, vacuum distilling at low temperatures in the presence of water, and recovering the purified tertiary alkyl hydroperoxide as a bottoms stream. Such distillation methods are deficient in that they do not permit complete separation of the tertiary hydroperoxide from the primary and secondary hydroperoxides, since these contaminants tend to co-distill with the desired product.

U.S. Pat. No. 4,584,413 teaches another method for the removal of primary and secondary hydroperoxides and involves treating the tertiary hydroperoxide with a hydroxide or oxide of an alkali metal or alkaline earth metal so as to preferentially decompose the undesired isomeric hydroperoxides. Although this process is effective, it does result in a significant loss of the desired tertiary hydroperoxide since the base-catalyzed decomposition is not completely selective. For commercial purposes, it would be desirable to minimize the loss of the tertiary hydroperoxide as much as possible.

The process of this invention avoids the disadvantages of the prior art in that it permits substantially complete removal of primary and secondary hydroperoxides from tertiary hydroperoxide compositions without significant decomposition of the desired tertiary hydroperoxide.

This invention provides a method for purifying a tertiary hydroperoxide composition containing undesired primary and secondary hydroperoxide contaminants which comprises the steps of (A) contacting the tertiary hydroperoxide composition with (a) a basic compound selected from the group consisting of alkali metal oxides, alkali metal hydroxides, alkali metal carbonates, alkali metal bicarbonates, alkaline earth oxides, alkaline earth hydroxides, alkaline earth carbonates, alkaline earth bicarbonates, and amines and (b) a carboxylic acid derivative selected from the group consisting of anhydrides, esters, acid halides and amides, and (B) separating said tertiary hydroperoxide containing substantially reduced amounts of undesired primary and secondary hydroperoxide contaminants.

The selective decomposition of primary and secondary hydroperoxide contaminants contained in a tertiary hydroperoxide composition which is accomplished by the method of this invention is believed to result from the base-catalyzed reaction of the primary and secondary hydroperoxides with the carboxylic acid derivative. The peroxyester adducts thus formed readily decompose to give ketones or aldehydes which may be easily separated from the purified tertiary hydroperoxide. The thermal instability of peroxyester adducts derived from primary and secondary hydroperoxides is well known [see G. Gouillon et al, The Chemistry of Peroxides, S. Patai, Ed., p. 299, Wiley, 1983]Although the tertiary hydroperoxide may also react with the carboxylic acid derivative, the resulting tertiary peroxyester adduct cannot decompose in a manner analogous to the peroxyester adducts of the primary and secondary hydroperoxides since it does not have a hydrogen alpha to the peroxyester bond. Instead, the tertiary peroxyester adduct may be hydrolyzed to regenerate the tertiary hydroperoxide. As a result, minimal loss of the tertiary hydroperoxide takes place.

Another factor which is believed to favor the selective removal of the primary and secondary hydroperoxide contaminants is the higher acidity of these species compared to tertiary hydroperoxides [see A. J. Everett et al, Trans. Faraday Soc. 49, 410 (1953)]. The higher acidity results in an enhanced reactivity of the hydroperoxide impurities towards the carboxylic acid derivative under the basic conditions of the process of this invention. This enhancement of reactivity results in preferential reaction of the primary and secondary hydroperoxides even when they are present at low levels in the tertiary hydroperoxide composition.

Without intending to limit the invention to a particular theory, the mechanism by which the process of this invention is believed to operate may be illustrated as indicated in Reaction Schemes 1 and 2. In this example, the tertiary hydroperoxide is tertiary butyl hydroperoxide (TBHP), the hydroperoxide impurity is sec-butyl hydroperoxide (SBHP), and the mixture of the two hydroperoxides is treated with an anhydride (A) and base. Peroxyester 1 in Reaction Scheme 1 cannot undergo the second reaction step to yield a ketone as shown in Reaction Scheme 2 since, unlike peroxyester 2, it does not have a hydrogen alpha to the peroxy bond. This proposed mechanism and the specific hydroperoxides given as examples therein are not intended to limit in any respect the scope of this invention. Further embodiments of the invention will become apparent to those skilled in the art from the following detailed description, examples, and claims.

Reaction Scheme 1

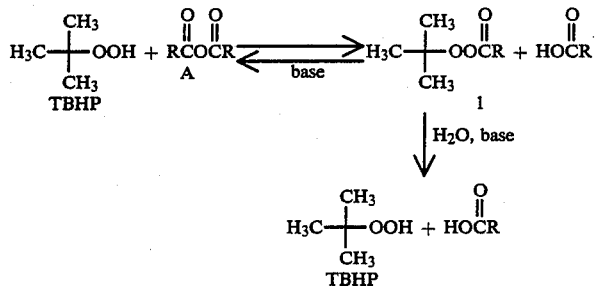

Reaction Scheme 2

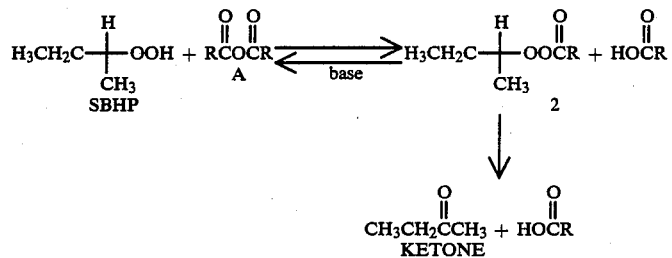

The tertiary hydroperoxide to be purified in accordance with the process of the present invention may be any suitable organic hydroperoxide which does not possess a hydrogen attached to the same carbon as the hydroperoxy group. Examples of suitable tertiary hydroperoxides include tertiary amyl hydroperoxide and cumene hydroperoxide. Tertiary butyl hydroperoxide is a particularly preferred hydroperoxide and may be obtained by methods well known in the art. For example, liquid phase oxidation of isobutane with an oxygen-containing gas may be used to generate the tertiary butyl hydroperoxide, as disclosed in U.S. Pat. No. 2,845,461. After removal of the unreacted isobutane, the crude oxidate recovered from the oxidizer is comprised of about 40 to 65 weight percent tertiary butyl hydroperoxide, about 30 to 55 weight percent tertiary butyl alcohol, and about 5 to 10 weight percent of other oxidation by-product, including the primary and secondary hydroperoxides to be removed in accordance with the process of the invention.

The conventional process for recovering the desired tertiary butyl hydroperoxide product revealed in U.S. Pat. No. 3,449,217 and 3,864,216 requires neutralization of the isobutane-free oxidate with base followed by distillation in the presence of a diluent vapor such as nitrogen. The tertiary butyl alcohol is removed, together with most of the low boiling oxidation by-products, by azeotropic distillation with water. Azeotropic distillation is continued to obtain another fraction which contains the tertiary butyl hydroperoxide. The hydroperoxide fraction is subjected to further distillation to yield a composition containing 65 to 75 percent t-butyl hydroperoxide in water. The undesired primary and secondary hydroperoxides are carried over head with the tertiary hydroperoxide and thus remain as impurities in the tertiary butyl hydroperoxide composition. In general, the concentration of these other hydroperoxides ranges from about 0.8 to 2.8 percent based on the tertiary hydroperoxide present.

The tertiary butyl hydroperoxide composition to be purified by the process of the present invention may comprise the oxidate obtained after isobutane oxidation following removal of the unreacted isobutane, or the "bottoms" fraction remaining after azeotropic distillation of the tertiary butyl alcohol from the oxidate. Alternatively, the 65 to 75 weight percent tertiary butyl hydroperoxide solution recovered as a distillate following distillation of the "bottoms" fraction may be employed in the process of this invention. Other tertiary hydroperoxide compositions prepared by analogous methods may also be purified in accordance with this invention.

Any suitable carboxylic acid derivative can be used in the purification according to this invention, provided it does not contain a functional group with an acidic portion. Examples of suitable carboxylic acid derivatives include anhydrides, acid chlorides, esters, and amides. All of these carboxylic acid derivatives may react with the primary and secondary hydroperoxide impurities in the tertiary hydroperoxide to form peroxyester adducts of the type shown in FIG. 2. Acid anhydrides and acid chlorides are preferred due to their high reactivity. Anhydrides such as maleic anhydride and acetic anhydride are particularly preferred.

The amount of carboxylic acid derivative used in the process of this invention will depend on the concentration of the primary and secondary hydroperoxide impurities in the tertiary hydroperoxide product to be purified and the level of those impurities which is desired in the final product. Typically, about 0.3 to 5.0 milliequivalents of carboxylic acid derivative per gram of total hydroperoxide present is sufficient to reduce the concentration of the primary and secondary hydroperoxides by approximately 80%.

Any basic compound which serves to catalyze the reaction between the carboxylic acid derivative and the primary and secondary hydroperoxide may be used in the process of the invention. Suitable basic compounds include strong bases such as alkali metal or alkaline earth hydroxides, and alkali metal or alkaline earth oxides as well as weaker bases such as alkali metal or alkaline earth carbonates, alkali metal or alkaline earth bicarbonates, and amines. Tertiary amines, including synthetic exchange resins containing tertiary amine functional groups, are preferred amines. Examples of particularly preferred basic compounds include potassium hydroxide and sodium hydroxide.

The amount of basic compound employed in the process of this invention should be sufficient to catalyze the reaction between the hydroperoxide impurities and the carboxylic acid derivative. The preferred amount of basic compound to be used will range from 1.5 to 3.5 milliequivalents of basic compound per milliequivalent of carboxylic acid derivative. The amount of basic compound required will generally be lower than a strong base such as sodium hydroxide rather than a weak base such as a tertiary amine is used.

In accordance with the process of this invention, the tertiary hydroperoxide may be contacted with the carboxylic acid derivative and basic compound at any suitable temperature. The exact temperature is not critical as the relative rate of decomposition and the overall percent decomposition of the primary and secondary hydroperoxides are not greatly influenced by temperature. In general, the reaction may be carried out at a temperature of from 20° C. to 175° C. The temperature range of from 30° C. to 80° C. is preferred. The rate of reaction of the carboxylic acid derivative is generally so rapid at these temperatures that the contact time of the reactants does not greatly affect the overall percent decomposition of the primary and secondary hydroperoxides. Substantial decomposition of these impurities is normally achieved within 30 seconds to 1 hour, preferably 1 to 30 minutes. Longer contact times may be employed if desired since the process of this invention results in minimal loss of tertiary hydroperoxide in contrast to the prior art methods.

The tertiary hydroperoxide composition purified in accordance with the invention may be recovered and separated from the ketone and aldehyde by-products derived from the primary and secondary hydroperoxides by any suitable method. Such methods are well known in the art and include, for example, liquid-liquid extraction and azeotropic distillation. Since the basic compound is not consumed in the reaction process, except for the small amount which is used to neutralize any organic acid which may be present, the basic compound may be re-used after recovery of the tertiary hydroperoxide to purify additional crude tertiary hydroperoxide. Additional quantities of the carboxylic acid derivative should be added to replace that amount which reacted previously with the primary and secondary hydroperoxides.

The following examples are given in order to further demonstrate the process of the invention.

EXAMPLES

Preparation of Crude Tertiary Butyl Hydroperoxide Samples—General

A. Oxidate Samples

Mixtures containing tertiary butyl alcohol (ca. 55%), tertiary butyl hydroperoxide (ca. 42%), and primary and secondary hydroperoxide impurities (ca. 1% total) were prepared by isobutane oxidation as described in U.S. Pat. No. 2,845,461 (incorporated herein by reference).

B. "Bottoms" Samples

Mixtures containing water (ca. 88%), tertiary butyl hydroperoxide (7-10%), primary and secondary hydroperoxide impurities (0.02-0.2% total), and sodium hydroxide (ca. 1 meq/g) were obtained as the "bottoms" from the fractional distillation of an isobutane oxidate admixed with caustic and water as described in U.S. Pat. No. 3,864,216 (incorporated herein by reference).

EXAMPLE 1

This example demonstrates the substantially complete removal of primary and secondary hydroperoxides from a tertiary hydroperoxide composition by the process of the invention. A "bottoms" sample (202 g) prepared as described in B above and containing 7.5 wt. % TBHP and 0.086 wt. % of primary and secondary hydroperoxide impurities was charged into a flask. Sodium hydroxide (33%, 5.17 g) was added, the temperature of the mixture quickly brought to 80° C., and 2.1 grams of maleic anhydride charged into the reactor. The total primary and secondary hydroperoxide concentration was reduced to 0.021 wt. % after 30 minutes while the tertiary butyl hydroperoxide concentration was 7.3 wt. %. These results represent a 75% reduction in the hydroperoxide impurities and only a 3% loss of the desired tertiary butyl hydroperoxide.

Thereafter, the tertiary butyl hydroperoxide was separated and concentrated by azeotropic distillation. The upper layer of the distillate contained 68.9% tertiary butyl hydroperoxide and 0.16 wt. % primary and secondary hydroperoxide.

EXAMPLES 2-4

These examples demonstrate both the high rate of reaction of the hydroperoxide impurities and the insensitivity to the temperature of the reaction at equivalent levels of added maleic anhydride and sodium hydroxide. In each example, 46.6 grams of a "bottoms" sample prepared as described in B above were charged into a reactor with 3.5 grams 33% aqueous sodium hydroxide and 0.9 grams maleic anhydride. As indicated in Table I, each example used a different reactor temperature. After ten minutes the level of primary and secondary hydroperoxides was measured, with the results shown in Table I.

TABLE I

| | Example No. | | |
|---|---|---|---|
| | 2 | 3 | 4 |
| Reactor Temp., °C. | 50.3 | 65.2 | 77.5 |
| % Reduction in 1° and 2° Hydroperoxide Content | 54 | 50 | 50 |

EXAMPLE 5

This example demonstrates the removal of primary and secondary hydroperoxide impurities from a tertiary butyl hydroperoxide composition containing tertiary butyl alcohol by the process of this invention. 11.25 grams of an oxidate sample prepared as described in A above, 46.69 grams of an 8 wt. % aqueous tertiary butyl alcohol solution, 3.25 grams aqueous 33% sodium hydroxide and 0.91 grams maleic anhydride were charged into a reactor at 63° C. The hydroperoxide impurities were reduced after 10 minutes from an initial value of 0.12 wt. % to a value of 0.04 wt. % (67% reduction). The initial concentration of tertiary butyl hydroperoxide was 7.6 wt. % of the mixture. After 10 minutes and after 30 minutes at 63° C. the concentration of tertiary butyl hydroperoxide was 7.6 wt. %, indicating that none of the desired tertiary butyl hydroperoxide was lost under these conditions.

CONTROL EXAMPLE 6

This example demonstrates that without the maleic anhydride treatment under alkaline conditions the level of the hydroperoxide impurities remains relatively high. An experiment conducted under conditions similar to Example 1, but without the addition of sodium hydroxide and maleic anhydride, yielded a upper phase following azeotropic distillation containing 67.8% tertiary butyl hydroperoxide and 0.37% hydroperoxide impurities.

CONTROL EXAMPLE 7

This example demonstrates the necessity of using a basic compound in combination with an anhydride in order to reduce the levels of hydroperoxide impurities in a tertiary butyl hydroperoxide composition. 25.1 grams of an oxidate sample prepared as described in A above and 0.5 gram maleic anhydride were charged into a reactor at 60° C. After reacting for 30 minutes, the total concentration of the primary and secondary hydroperoxides was 0.64 wt. %, compared to an initial concentration of 0.65 wt. %. This represents a 2% reduction in the concentration of the hydroperoxide impurities.

COMPARATIVE EXAMPLE 8

This example demonstrates that in a short period of time, treatment of a tertiary butyl hydroperoxide with base alone does not reduce the levels of the undesired primary and secondary hydroperoxides to the same extent as when an anhydride is added with the base (Example 1). This example also shows that higher losses of the desired tertiary butyl hydroperoxide result when only base is used. It should additionally be noted that the level of base used in Example 1 (0.0084 g/g sample) was less than that used in this example (0.025 g/g sample), indicating that the substantial reduction in hydroperoxide impurity levels in Example 1 was not due to the action of the base alone.

83.95 grams of a "bottoms" sample prepared as described in B above and 6.40 grams of 33% sodium hydroxide were charged into a reactor and brought quickly to 61° C. After 50 minutes, the concentration of primary and secondary hydroperoxide was 0.0655% (compared to 0.0746% initially), and the concentration of tertiary butyl hydroperoxide was 7.0% (compared to 7.5% initially). This represents a 12% reduction in the detrimental hydroperoxide impurities and a 7% reduction in the tertiary butyl hydroperoxide.

I claim:

1. A process for purifying a tertiary hydroperoxide composition comprised of a tertiary hydroperoxide and an undesired primary or secondary hydroperoxide contaminant which comprises the steps of:
   (A) contacting the tertiary hydroperoxide composition with
      (a) a basic compound selected from the group consisting of alkali metal oxides, alkali metal hydroxides, alkali metal carbonates, alkali metal bicarbonates, alkaline earth oxides, alkaline earth hydroxides, alkaline earth carbonates, alkaline earth bicarbonates, and amines, and
      (b) a carboxylic acid derivative selected from the group consisting of anhydrides, esters, acid halides, and amides
   at a temperature of between about 20° C. and 175° C. and for a period of from about 30 seconds to 1 hour to decompose said primary or secondary hydroperoxide contaminant, and
   (B) separating a purified tertiary hydroperoxide composition from said basic compound, said carboxylic acid derivative, and said primary or secondary hydroperoxide decomposition product.

2. The process of claim 1 wherein said tertiary hydroperoxide is tertiary butyl hydroperoxide.

3. The process of claim 1 wherein said basic compound is an alkali metal hydroxide.

4. The process of claim 1 wherein said tertiary hydroperoxide composition is contacted with from about 0.3 to 5.0 milliequivalents of said carboxylic acid derivative per gram of total hydroperoxide present.

5. The process of claim 1 wherein said tertiary hydroperoxide composition is contacted with from about 1.5 to 3.5 milliequivalents of said basic compound per milliequivalents of said carboxylic acid derivative.

6. The process of claim 1 wherein said carboxylic acid derivative is an anhydride.

7. The process of claim 6 wherein said anhydride is maleic anhydride.

8. The process of claim 1 wherein said tertiary hydroperoxide composition is separated by liquid-liquid extraction.

9. The process of claim 1 wherein said tertiary hydroperoxide composition is separated by azeotropic distillation.

10. The process of claim 1 wherein said tertiary hydroperoxide composition additionally comprises a tertiary alcohol.

11. The process of claim 1 wherein said tertiary hydroperoxide composition additionally comprises water.

12. A process for purifying a tertiary butyl hydroperoxide composition comprising tertiary butyl hydroperoxide and an undesired primary or secondary hydroperoxide contaminant which comprises the steps of:
   (A) contacting the tertiary butyl hydroperoxide composition with
      (a) from about 0.3 to 5.0 milliequivalents of a carboxylic acid anhydride per gram of total hydroperoxide present and
      (b) from about 1.5 to 3.5 milliequivalents of an alkali metal hydroxide per milliequivalent of said carboxylic acid anhydride at a temperature of between about 20° C. and 175° C. for a period of from about 30 seconds to 1 hour to decompose said primary or secondary hydroperoxide contaminant; and
   (B) separating a purified tertiary butyl hydroperoxide composition from said carboxylic acid anhydride, said alkali metal hydroxide, and primary or secondary hydroperoxide decomposition product.

13. The process of claim 12 wherein said alkali metal hydroxide is sodium hydroxide.

14. The process of claim 12 wherein said carboxylic acid anhydride is maleic anhydride.

15. The process of claim 12 wherein said tertiary butyl hydroperoxide composition is separated by liquid-liquid extraction.

16. The process of claim 12 wherein said tertiary butyl hydroperoxide composition is separated by azeotropic distillation.

17. A process for purifying a tertiary butyl hydroperoxide composition comprising tertiary butyl hydroperoxide and an undesired primary or secondary hydroperoxide contaminant which comprises the steps of:
  (A) contacting the tertiary butyl hydroperoxide composition with
    (a) from about 0.3 to 5.0 milliequivalents of maleic anhydride per gram of total hydroperoxide present and
    (b) from about 1.5 to 3.5 milliequivalents of sodium hydroxide per milliequivalent of maleic anhydride at a temperature of between about 30° C. to 80° C. for a period of from about 1 to 30 minutes to decompose said primary or secondary hydroperoxide contaminant; and
  (B) separating a purified tertiary butyl hydroperoxide composition from said maleic anhydride, said sodium hydroxide, and said primary or secondary hydroperoxide decomposition product.

18. The process of claim 17 wherein said tertiary butyl hydroperoxide composition is separated by liquid-liquid extraction.

19. The process of claim 17 wherein said tertiary butyl hydroperoxide composition is separated by azeotropic distillation.

* * * * *